United States Patent [19]

Voege

[11] 4,366,947

[45] Jan. 4, 1983

[54] CALIBRATED GAS-METERING APPARATUS

[75] Inventor: Clayton B. Voege, Indianapolis, Ind.

[73] Assignee: AMP Corporation, Indianapolis, Ind.

[21] Appl. No.: 265,625

[22] Filed: May 20, 1981

[51] Int. Cl.³ .................... F16K 3/32; F16K 51/00; B23P 19/02

[52] U.S. Cl. .................... 251/206; 251/208; 138/45; 73/3; 29/525

[58] Field of Search ............ 251/206, 205, 208; 73/3; 138/45; 137/DIG. 2; 29/157.1 R, 525

[56] References Cited

U.S. PATENT DOCUMENTS

| | | | |
|---|---|---|---|
| 1,980,144 | 11/1934 | Siena et al. .................... | 137/DIG. 2 |
| 2,621,012 | 12/1952 | Graham ........................... | 138/45 X |
| 4,241,896 | 12/1980 | Voege ............................. | 251/206 |

FOREIGN PATENT DOCUMENTS

| | | | |
|---|---|---|---|
| 459389 | 9/1950 | Italy ............................ | 137/DIG. 2 |
| 309 | 1/1914 | United Kingdom ............. | 251/205 |

Primary Examiner—Arnold Rosenthal
Attorney, Agent, or Firm—Jenkins, Coffey, Hyland, Badger & Conard

[57] ABSTRACT

A calibrated gas-metering valve is disclosed which includes a two-part valve body having a gas inlet, a gas outlet, and a metering element therebetween. The metering element has a first and a second hole therein, which first and second hole intersect and together define a passage for gas flow from the gas inlet to the gas outlet. A ball of a diameter approximately equal to the diameter of the first hole is press-fitted into the first hole so as to be positioned therein solely by the fitting engagement of its surface with the wall of the first hole. The ball is located adjacent the intersection of the first and second holes so as to define a region in the passage having a cross-sectional area less than the cross-sectional area of either the first or second holes. The position of the ball with respect to the intersection of the holes is fixed to achieve the desired gas-metering rate.

15 Claims, 4 Drawing Figures

CALIBRATED GAS-METERING APPARATUS

This invention relates to calibrated gas-metering devices, and particularly those devices applicable to provide a precisely calibrated therapeutic oxygen flow in a portable oxygen supply kit adapted to be carried by an ambulatory patient to supply a prescribed rate of oxygen to such patient. The invention also relates to a selective control valve which is used in such metering devices to selectively provide a plurality of accurate oxygen flow rates.

Oxygen supply kits for ambulatory patients are known and in use. They include an indexing control valve which is movable to a plurality of positions, each providing a different flow rate, for example, 1, 2, 3, 4, and 5 liters per minute. Such flow rates are obtained by passing the gas at a regulated pressure through metering orifices in a metering disk. In one application, such rates required metering holes having diameters, respectively, of approximately 0.006, 0.009, 0.011, 0.013, and 0.015 inches. The orifices had been formed by drilling these small holes in the metering disk or inserts in the metering disk mechanically or by an EDM process. Such drilling does not provide sufficient accuracy, and when the EDM process is employed, it is necessary to allow a margin of error of plus or minus 10% of the desired flow rate. An example of such an apparatus is to be found in U.S. Pat. No. 3,949,966.

In accordance with my prior invention, U.S. Pat. No. 4,241,896, a calibrated gas-metering orifice was formed by first forming a hole in a valve body, then progressively press-fitting into the hole a cylindrical plug having in its surface a groove which opened through the entering end of the plug and was of progressive decreasing cross-sectional area toward the opposite end of the plug, so that the groove formed, with the wall of the hole, an opening of a size which depended upon the depth to which the cylindrical plug was inserted into the hole. The gas flow rate through such an orifice was monitored as the cylindrical plug was pressed into the hole and the plug was stopped at a position which gave the desired flow rate.

While that invention provided a much more accurate metering orifice, and reduced the necessary margin of error to the order of plus or minus 1%, the apparatus was difficult to manufacture due to the very small size of the components involved. For example, the cross-sectional area approximately equal to that of a 0.015 inch diameter hole was provided by scribing a V-shaped groove on the cylindrical surface of the plug, the groove having a 60° included angle between its side walls and a depth of 0.010 inch. The groove also had a relatively long taper so that its area varied at a slow rate lengthwise of the plug so that a fine adjustment could be achieved as the cylindrical plug was pressed into the hole. However, the cylindrical form of the plug made the initiation of the press fitting rather difficult without damaging the plug, and particularly the V-shaped groove in the side of the plug.

In accordance with the present invention, there is provided an apparatus of similar function but of dramatically different design which is much easier to manufacture yet achieves the accuracy and reliability of my prior invention. A gas-metering valve according to the present invention includes a valve body having an inlet and an outlet with a dividing wall therebetween, the dividing wall including a metering element having a first and second hole therein, which first and second holes intersect and together define a passage for gas flow from the inlet to the outlet. A ball of a diameter approximately equal to the diameter of the first hole is press-fitted into the first hole so as to be positioned therein solely by the fitting engagement of its surface with the wall of the first hole. The ball is positioned adjacent the intersection of the first and second holes so as to define a region in the passage having a cross-sectional area less than the cross-sectional area of either the first or second hole. By manipulating the position of the ball while monitoring the flow of gas through the passage, the ball can be positioned at a location which will achieve the desired gas flow rate. Desirably, the first hole is several times larger and preferably four or more times larger than the second hole. On the one hand, this facilitates handling and insertion of the ball, and on the other hand, facilitates formation of a gas passage providing the desired small and accurate gas flow rate. A plurality of such first and second holes can be provided, each set of a first and a second hole defining a separate passage for the metered flow of gas from the inlet to the outlet. The passages thus defined are positionable in communication with the gas inlet such that only one such passage can permit the flow of gas therethrough at any one instant in time. A detent means can be provided for assuring appropriate alignment of one of said passages with respect to the gas inlet.

In the preferred embodiment, the metering element comprises a cylinder, and the first holes are arranged in a circle about the axis of rotation of the cylinder and extend linearly through the cylindrical element parallel to the axis of rotation. The second holes extend radially from the cylindrical surface of the element to the point of intersection with the first holes. The balls are press-fit from one face of the cylinder to the point of intersection of the first and second holes, each ball being positioned at a slightly different location so as to achieve a different flow rate through each passage thus formed.

To assure proper alignment of the cylindrical metering element, a circular race is provided in one end of the element, the race being in registry with the circular arrangement of first holes. A detent means comprising a spring-biased ball is arranged in rolling frictional engagement in the race to effect an arresting action in any rotation of the cylindrical element, the detent means being so situated as to cause selected alignment of a single first and second hole pair to provide a passage between the inlet and outlet of the gas-metering valve.

The accompanying drawings illustrate the invention and show a preferred embodiment exemplifying the best mode of carrying out the invention as presently perceived. In such drawings.

Figure 1:
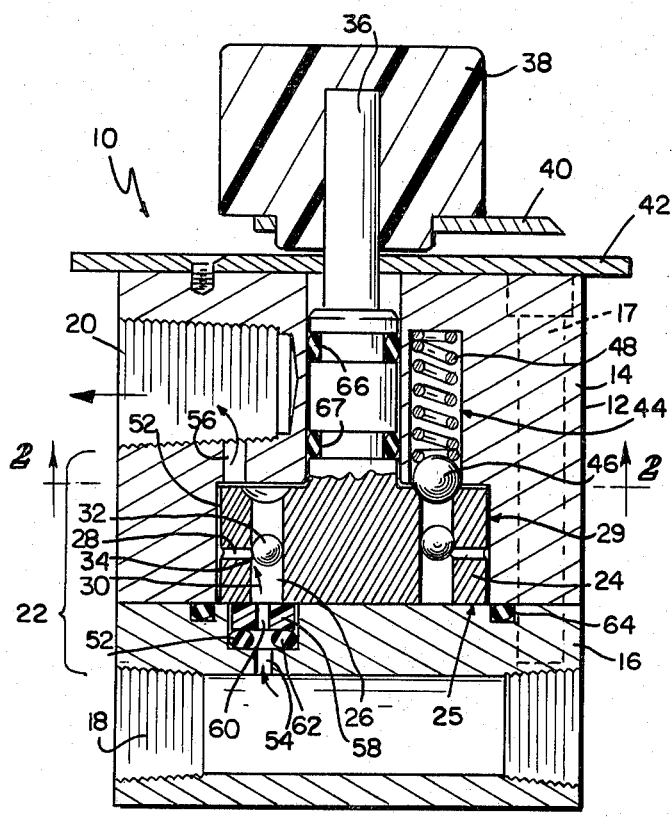
FIG. 1 is an axial section of a calibrated metering apparatus according to the present invention.
Figure 3:
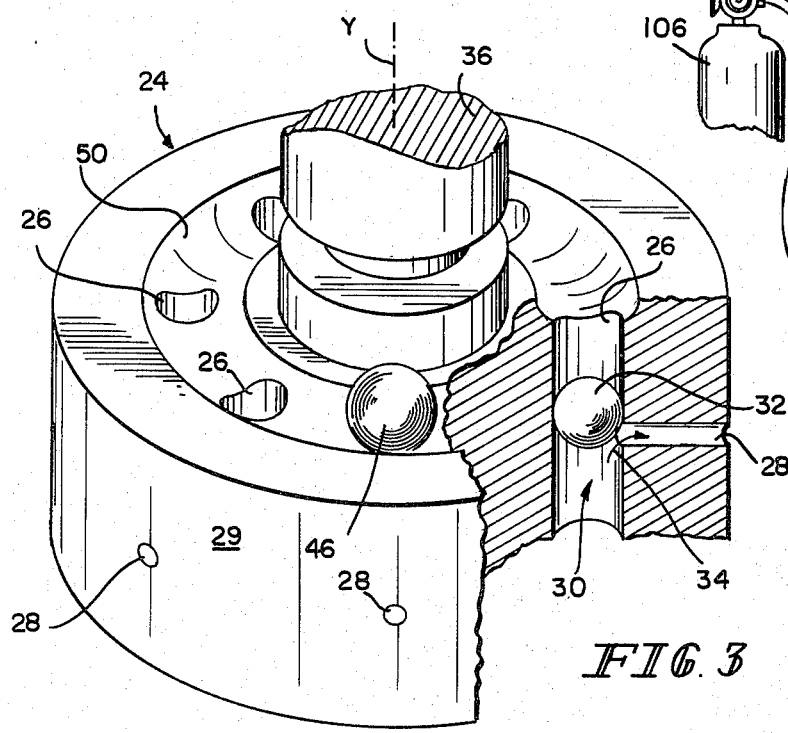
Figure 4:
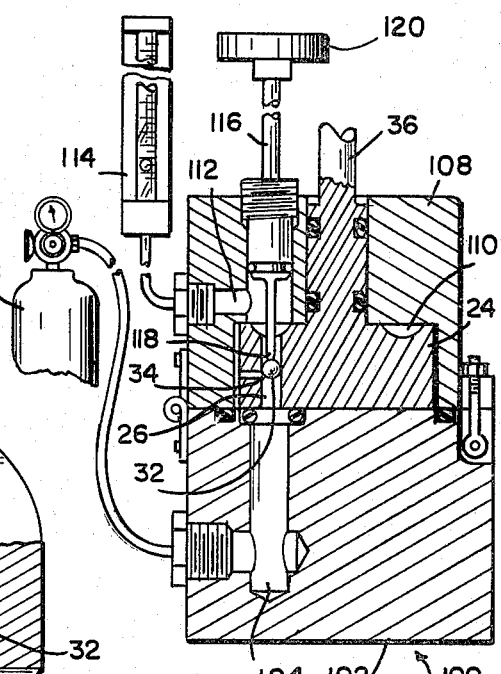

FIG. 3 is a perspective view of the metering element employed in the apparatus shown in FIG. 1, the metering element shown partially in section so as to illustrate the positioning of the ball within a first hole adjacent an intersection of a first and second hole to thereby define a gas passageway; and FIG. 4 is a diagrammatic view of an apparatus for calibrating a metering element of the type shown in FIG. 3.

Figure 2:
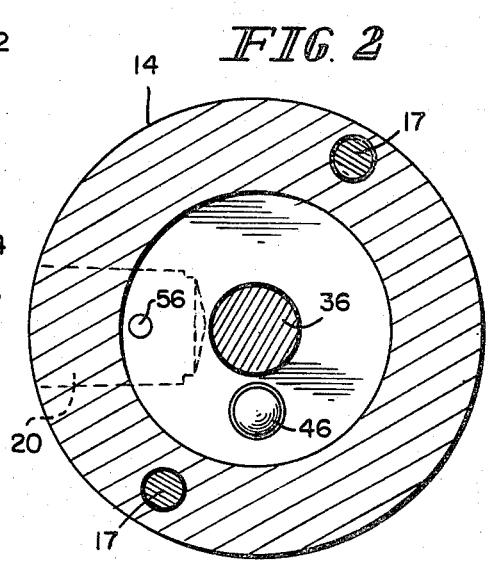
FIG. 2 is a transverse section of the apparatus illustrated in FIG. 1, taken on line 2—2.

The valve 10 shown in FIGS. 1-3 comprises a valve housing 12 illustrated to include a top body 14 and a bottom body 16 secured to the top body 14 by screw-threaded studs 17. The valve housing 12 includes a gas inlet 18 and a gas outlet 20 separated by a dividing wall region 22 including a gas-metering element 24. The gas-metering element includes a first hole 26 and a second hole 28 which intersects the first hole 26. By way of example, the first hole may be of 0.124 inch diameter and the second of 0.020 inch diameter. The first hole 26 and second hole 28 together define a passage 30 for gas to flow from the gas inlet 18 to the gas outlet 20. A ball 32 of a diameter approximately equal to the diameter of the first hole 26 of 0.125 inch diameter in the above example is press-fitted into the first hole 26 so as to be solidly positioned therein solely by the fitting engagement of its surface with the wall of the first hole 26. The ball 32 is positioned adjacent the intersection of the first hole 26 and second hole 28 so as to define a restricted opening or region 34 in the passage 30 having a cross-sectional area less than the cross-sectional area of either the first hole 26 or the second hole 28. It is this restricted region 34 which performs the metering function in the present gas-metering valve 10.

The metering element 24 shown is cylindrical in shape and includes a plurality of such first and second holes as more clearly shown in FIG. 3. The metering element is adapted to be selectively moved to a plurality of metering positions to selectively provide a series of different gas-flow rates. As shown, the first holes 26 are arranged in a circle about the axis of rotation Y, the holes 26 extending linearly through the cylindrical element 24 parallel to the axis of rotation Y. The second holes 28 extend radially from the cylindrical surface 29 of element 24 to the point of intersection of the second hole 28 with the first hole 26.

The element 24 is rotatable about axis Y by means of shaft 36 projecting axially upward beyond the upper surface of top body 14. A knob 38 is fixed to shaft 36, the knob 38 including an indicator means 40 which, together with appropriate markings on face plate 42, indicate the angular position of element 24.

The valve further comprises a detent means 44 for arresting the movement of the metering element 24 with respect to the valve body 12 so as to assure registry of one of the passages 30 with the gas inlet 18. The detent means 44 comprises a ball 46 and biasing spring 48 which forces the ball 46 into rolling frictional engagement with a circular race 50 provided on one end of the cylindrical valve element 24. The race 50 is in registry with the circular arrangement of first holes 26 such that when the biased ball 46 contacts the top of a first hole 26, the biased ball descends downward sufficient to releasably lockingly engage element 24 with respect to body 12.

The cylindrical element 24 is rotatably positioned within a chamber 52 which is situated between the gas inlet 18 and the gas outlet 20. A first aperture 54 is provided between the chamber 52 and the gas inlet 18. A second aperture 56 is provided between chamber 52 and gas outlet 20. The first aperture 54 includes a seal 58 in sliding contact with the gas-metering element 24, the seal having an opening 60 therethrough. The seal 58 is preferably composed of a material having a very low frictional coefficient as well as self-lubricating qualities such as tetrafluoroethylene or the like. An O-ring 62 backing the sliding seal 58 assures constant frictional engagement between the lower face 25 of gas-metering element 24 and the sliding seal 58. The chamber 52 is further sealed by O-ring 64 in an upper surface of the bottom body 16 surrounding the chamber 52 and by O-rings 66 and 67 surrounding shaft 36.

The metering element 24, as illustrated in FIG. 3, is calibrated with the aid of a calibration jig 100 illustrated in FIG. 4. The jig includes a lower body portion 102 with a gas inlet 104 connected to a regulated supply of gas 106. The jig 100 also includes an upper body portion 108 including a chamber 110 into which a gas-metering element 24 according to the present invention can be placed. Communicating with chamber 110 is gas outlet 112 which is connected to a manometer 114 which is calibrated in appropriate units for use by an operator of jig 100. A screw-threaded plunger 116 in jig body 108 extends downward in alignment with first hole 26 in the gas-metering element 24. The lower end 118 of screw-threaded plunger 116 contacts ball 32. The rotation of handle 120 of the screw-threaded plunger 116 causes end 118, and hence ball 32, to descend down first hole 26. The size of region 34 is calibrated by permitting gas at a known pressure from regulated gas source 106 to pass into gas inlet 104 through region 34 to gas outlet 112 and thence to manometer 114. The operator of jig 100 then advances the screw-threaded plunger 116 by turning handle 120, thus causing ball 32 to descend down hole 26 until the rate of gas flow through region 34 reaches the desired level as measured on manometer 114. This operation is repeated for each pair of first and second holes 26 and 28 to provide the desired flow rates at the several settings of the metering element 24.

While the invention has been described with reference to the presently preferred and illustrated embodiment thereof, it is not intended that the invention be unduly limited by this description of the preferred embodiment, and instead it is intended that the invention be defined by the means and their obvious equivalents set forth in the following claims.

What is claimed is:

1. A calibrated gas-metering valve comprising a valve body having a gas inlet, a gas outlet, and a dividing wall therebetween, the dividing wall having a metering element including at least a first and a second hole therein, which first and second hole intersect and together define a passage for gas flow from the gas inlet to the gas outlet, and a ball of a diameter approximately equal to the diameter of the first hole press-fitted in the first hole so as to be solidly positioned therein by the fitting engagement of its surface with the wall of the first hole, the ball being positioned adjacent the intersection of the first and second holes so as to define a region in the passage having a cross-sectional area less than the cross-sectional area of either the first or second hole.

2. A calibrated gas-metering valve as in claim 1 in which said first hole is several times larger than said second hole.

3. A calibrated gas-metering valve as in claim 2 in which said first hole is four or more times larger than said second hole.

4. The calibrated gas-metering valve of claim 1 or 3 wherein said metering element has a plurality of said first and second holes defining a like plurality of passages for gas flow from the gas inlet to the gas outlet, and said metering element is movable with respect to the gas inlet so as to permit only one of said plurality of passages to be positioned in communication with the gas inlet at any one instant in time.

5. The calibrated gas-metering valve of claim 4 further comprising detent means for arresting the movement of said dividing wall with respect to said gas inlet so as to assure registry of one of said plurality of passages with the gas inlet.

6. The calibrated gas-metering valve of claim 5 wherein said detent means comprises a biased ball in frictional engagement with said dividing wall, the biased ball at least partially engageable with one end of said plurality of first holes to effect the arresting action.

7. A gas-metering element adapted to be selectively moved to a plurality of metering positions for selectively providing a series of different gas flow rates,
a series of first and second intersecting holes in said element which together define a like series of passages adapted to be selectively positioned to control gas flow,
a like series of balls of a diameter approximately equal to the diameter of the first holes press-fitted in the first holes so as to be solidly positioned therein by the fitting engagement of their surfaces with the walls of the first holes, each ball being adjacent the intersection of the first and second holes so as to define a region having a cross-sectional area less than the cross-sectional area of either the first or second holes forming such passage, the series of regions defined within the series of passages being such as will give a series of different gas flow rates.

8. The gas-metering element of claim 7 wherein the element is cylindrical, the first holes being arranged in a circle about the axis of rotation and extending linearly through the cylindrical element parallel to the axis of rotation, and the second holes extend radially from the cylindrical surface of the element to the point of intersection with the first holes.

9. The gas-metering element of claim 8 further comprising a circular race in one end of the cylindrical element, the race being in registry with the circular arrangement of the first holes.

10. The gas-metering element of claim 8 wherein said element further comprises a stem projecting axially from one end of the cylindrical element for transmitting a rotational torque to said element to permit selective changes in orientation of the element.

11. A gas-metering valve for selectively providing a series of different calibrated gas flow rates therethrough comprising a valve body having a gas inlet, a gas outlet, a chamber situated between the gas inlet and gas outlet, a first aperture between the chamber and the gas inlet, and a second aperture between the chamber and the gas outlet,
a gas-metering element situated in the chamber and adapted to be selectively moved to a plurality of metering positions for selectively providing a series of different gas flow rates, a series of first and second intersecting holes in said element which together define a like series of passages adapted to be selectively positioned to control gas flow, a series of balls of a diameter approximately equal to the diameter of the first holes press-fitted in the first holes so as to be solidly positioned therein by the fitting engagement of their surfaces with the walls of the first holes adjacent the intersection of the first and second holes so as to define regions in the passages having cross-sectional areas less than the cross-sectional areas of either the first or second holes in which the regions occur, the series of regions defined within the series of passages being such as will give a series of different gas flow rates.

12. The gas-metering valve of claim 11 wherein one of the apertures between said chamber and the gas inlet or outlet further comprises a seal in sliding contact with the gas-metering element, the seal having an opening therethrough aligned with said series of passages for sealing said chamber against the transmission of gas therethrough except when the gas-metering element is oriented with one of said series of passages in registry with the opening through the seal.

13. The gas-metering valve of claim 12 wherein the element is cylindrical, the first holes being arranged in a circle about the axis of rotation and extending linearly through the cylinder element parallel to the axis of rotation, the second holes extending radially from the cylindrical surface of the element to the point of intersection with the first holes.

14. The gas-metering valve of claim 13 wherein said seal is in sliding contact with a planar face of said cylindrical element, the seal being situated between the gas inlet and the gas-metering element.

15. A gas-metering valve of claim 11 or 13 in which said first holes are several times larger than said second holes.

* * * * *